US008158793B2

(12) United States Patent
Lauterbach et al.

(10) Patent No.: US 8,158,793 B2
(45) Date of Patent: Apr. 17, 2012

(54) DEMETHYLATION OF 14-HYDROXY SUBSTITUTED ALKALOID DERIVATIVES

(75) Inventors: Erik Heinz Lauterbach, Suhr (CH);
Thomas Dinkel, Strengelbach (CH);
Sabrina Heller, Oftringern (CH);
Andreas Bertogg, Zurich (CH)

(73) Assignee: Siegfried Ltd., Zofingen (CH)

( * ) Notice: Subject to any disclaimer, the term of this patent is extended or adjusted under 35 U.S.C. 154(b) by 635 days.

(21) Appl. No.: 12/292,704

(22) Filed: Nov. 24, 2008

(65) Prior Publication Data
US 2009/0163717 A1 Jun. 25, 2009

Related U.S. Application Data

(63) Continuation-in-part of application No. 12/289,492, filed on Oct. 29, 2008, now Pat. No. 7,619,088.

(30) Foreign Application Priority Data
Nov. 26, 2007 (EP) .................................. 07121537

(51) Int. Cl.
*C07D 489/08* (2006.01)
*C07F 7/02* (2006.01)
(52) U.S. Cl. .......................................... 546/45; 546/14

(58) Field of Classification Search ................ 546/45, 546/14
See application file for complete search history.

(56) References Cited

U.S. PATENT DOCUMENTS
7,619,088 B2 * 11/2009 Lauterbach et al. ........... 546/45

FOREIGN PATENT DOCUMENTS
GB 1124441 8/1968
WO WO 2006/084389 A1 8/2006

OTHER PUBLICATIONS
Iijima, Ikuo et al., "Studies in the (+)-Morphinan Series. 5.[1] Synthesis and Biological Properties of (+)-Naloxone," Journal of Medicinal Chemistry, 1978, pp. 398-400, vol. 21 (4), American Chemical Society.

* cited by examiner

*Primary Examiner* — Charanjit Aulakh
(74) *Attorney, Agent, or Firm* — The Nath Law Group; Susanne M. Hopkins; Tanya E. Harkins

(57) ABSTRACT

The present invention is directed to a method for demethylating 14-hydroxy substituted alkaloid derivatives, in particular of 14-hydroxy-17-methyl-4,5-epoxymorphinane-6-on-derivatives. This is achieved by reacting a starting compound with a compound of general formula $R^1OOC-N=N-COOR^2$ in a suitable solvent.

28 Claims, 5 Drawing Sheets

DEMETHYLATION OF 14-HYDROXY SUBSTITUTED ALKALOID DERIVATIVES

Figure 1:
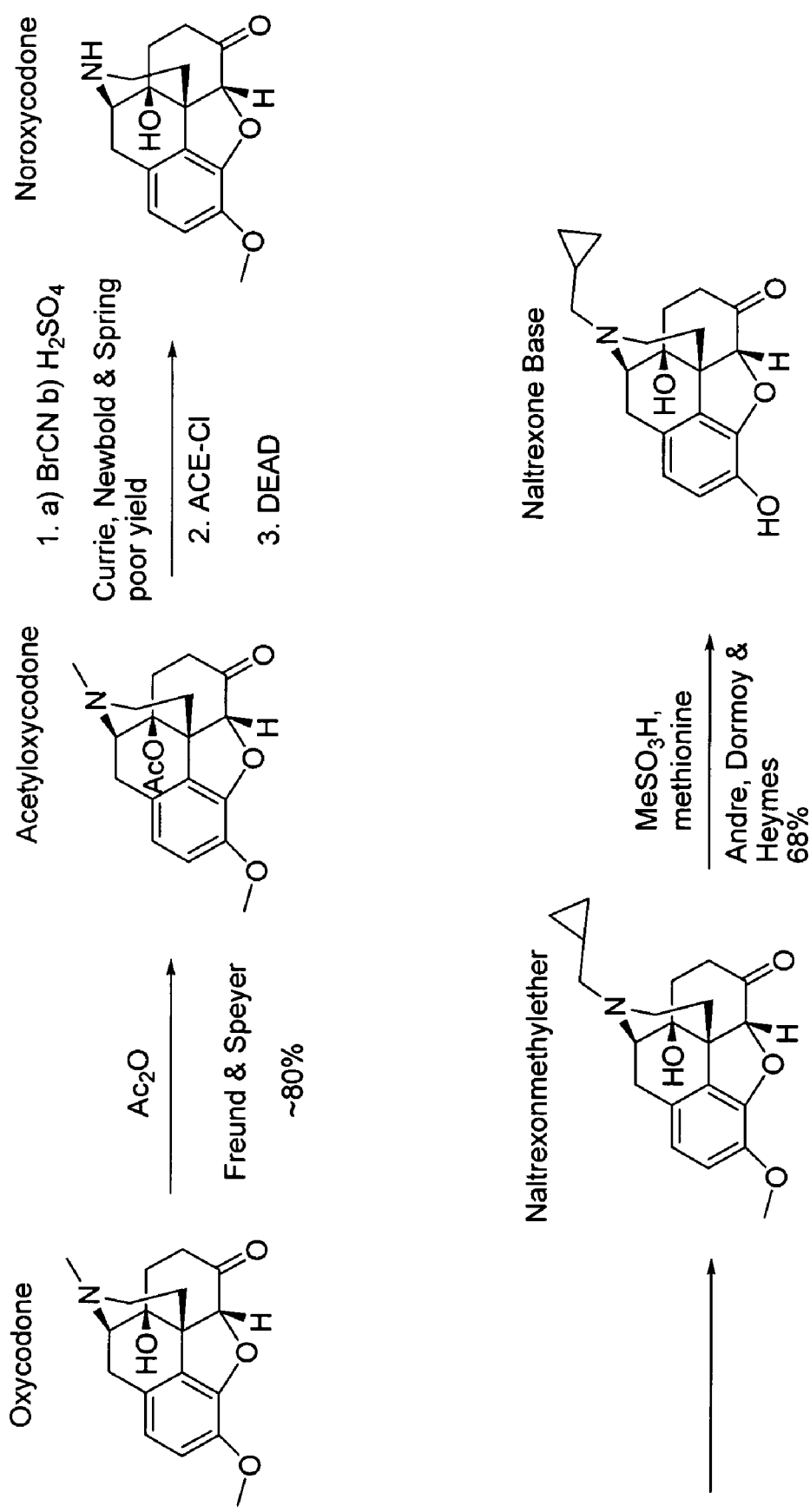

The present invention is directed to a method for demethylating 14-hydroxy substituted alkaloid derivatives, in particular of 14-hydroxy-17-methyl-4,5-epoxymorphinane-6-on-derivatives. This is achieved by reacting a starting compound with a compound of general formula $R^1OOC—N=N—COOR^2$ in a suitable solvent.

BACKGROUND OF THE INVENTION

Naltrexone is an opioid receptor antagonist used primarily in the management of alcohol dependence and opioid dependence. It is available on the market in form of its hydrochloric salt, i.e. naltrexone hydrochloride. Naltrexone and its active metabolite 6β-naltrexol are competitive antagonists at μ- and κ-opioid receptors, and to a lesser extent at δ-opioid receptors. The plasma halflife of naltrexone is about 4 hours, for 6-β-naltrexol 13 hours.

One important step in the synthesis of naltrexone is a demethylation step for removing the methyl group from the nitrogen atom of the alkaloid molecule, as it is present for example in oxycodone and oxymorphone.

One way to achieve this demethylation step is disclosed in GB-1,124,441. Therein, a process of removing a methyl group from a tertiary nitrogen atom of an alkaloid molecule is disclosed, comprising reacting the methylated compound with a lower alkyl azodicarboxylate, wherein the lower alkyl group has from 1-8 carbon atoms, for a time sufficient to bring about a reaction and to provide a demethylated alkaloid derivative. However, the patent specification is only related to alkaloid compounds, which do not carry an OH-group at C14 of the alkaloid backbone. For example, GB-1,124,441 is silent on how to perform a demethylation on oxycodone and oxymorphone, respectively.

The paper titled "Reactions of Azodicarboxylic Esters with Amines" of S. HOSZTAFI, Österreichische Apotheker-Verlagsges.m.b.H., Wien, 1987, describes the reactions of aliphatic and aromatic amines and alkaloids with azodicarboxylic esters.

Further documents are available which are related to the demethylation of alkaloids, for example, EP 0 295 783 discloses diethyl azodicarboxylate for demethylating alkaloids. On page 8 of the description, it is disclosed to use diethyl azodicarboxylate in acetonitrile for the N-dealkylation of a compound of the indicated formula. However, in the course of this reaction, a bridging group is introduced between 2N-atoms as it can be seen from formula (VII). Furthermore, EP 0 295 783 is not related to alkaloids having a 14-OH group.

The like, GB-1,179,479 discloses removing a methyl group by treatment with a di-lower alkyl azodicarboxylate, wherein the lower alkyl group has from 1-4 carbon atoms, followed by treatment of delute mineral acid. This reaction, however, is disclosed in the context of general formula (I) as indicated in GB-1,179,479, which does not possess a 14-OH group.

In the prior art, there are also chemical processes disclosed, which allow the demethylation of alkaloid compounds which are carrying an OH-group at C14. In these methods, however, the OH group is being protected in order to avoid a reaction with the usual demethylation agents.

For example, oxycodone may be reacted with $Ac_2O$ in order to achieve acetyloxycodone (having a protected OH-group) which is further converted by well-known demethylating agents ($BrCN/H_2SO_4$) to noroxycodone (which is demethylated).

The same step can be performed in the synthesis of noroxymorphone, starting from oxymorphone. There, oxymorphone is reacted with $Ac_2O$ resulting in a protected OH-group at C14 (oxymorphone diacetate). After reacting with BrCN and $H_2SO_4$, noroxymorphone is yielded. The conversion by means of BrCN is described in IIJIMA et al., "Studies in the (+)-Morphinan Series. 5. Synthesis and Biological Properties of (+)-Naloxone", Journal of Medicinal Chemistry, 1978, Vol. 21, No. 4.

However, there is not any disclosure in the art for a process for demethylating alkaloid derivatives which are carrying the 14-OH group, which 14-OH group is not being protected during the reaction. This might be due to the fact that conventional demethylating agents, such as BrCN, do not function under these circumstances as proper demethylating agents: The free OH group at C14 is too close to the cyanide and can perform a 5-exo-dig-cyclization which would not allow a proper performance of the reaction. See in this connection, CURRIE, A. C.; NEWBOLD, G. T. et al., Roy. Coll. Sci., Technol., Glasgow, UK, Journal of the Chemical Society, abstracts (1961), 4693-4700.

Further, see also GB-975,601, published in 1964. Here, it is disclosed that 14-acetoxy-N-cyanonorcodeine acetate may be produced by reacting 14-acetoxycodeine acetate with cyanogen bromide and may be converted to 14-hydroxynorcodeine by means of lithium aluminium hydride.

SUMMARY OF THE INVENTION

Therefore, there is a need remaining to provide a method of demethylating 14-OH substituted alkaloid derivatives, and in particular, oxycodone and oxymorphone without the need of protecting/deprotecting the 14-OH group. Furthermore, it is an object of the present invention to provide a method of demethylating alkaloid derivatives which is environment-friendly and allows a conversion of 14-OH-alkaloid derivatives to the respective nor-alkaloid-derivatives in a high yield.

These problems are solved by the subject-matter of the independent claim. Embodiments are set forth in the dependent claims.

By the present invention, for the first time, a way of demethylating alkaloid derivatives having a 14-OH group is provided without the need of protecting the OH group during the reaction. This, surprisingly, could be achieved by using azodicarboxylic acid dialkyl esters of general formula $R^1OOC—N=N—COOR^2$ in a suitable solvent. This is insofar surprising as the prior art teaches that the 14-OH group is too reactive for using the conventional demethylating agents as discussed above without having protected the 14-OH group before.

By the new process of demethylation, two additional steps can be avoided, i.e. protecting and deprotecting the 14-OH-group of the alkaloid derivative. Furthermore, by using azodicarboxylic acid dialkyl ester compounds as, for example, DIAD or DEAD, substances, which are potentially harmful to the environment (like BrCN) may be avoided.

Figure 2:
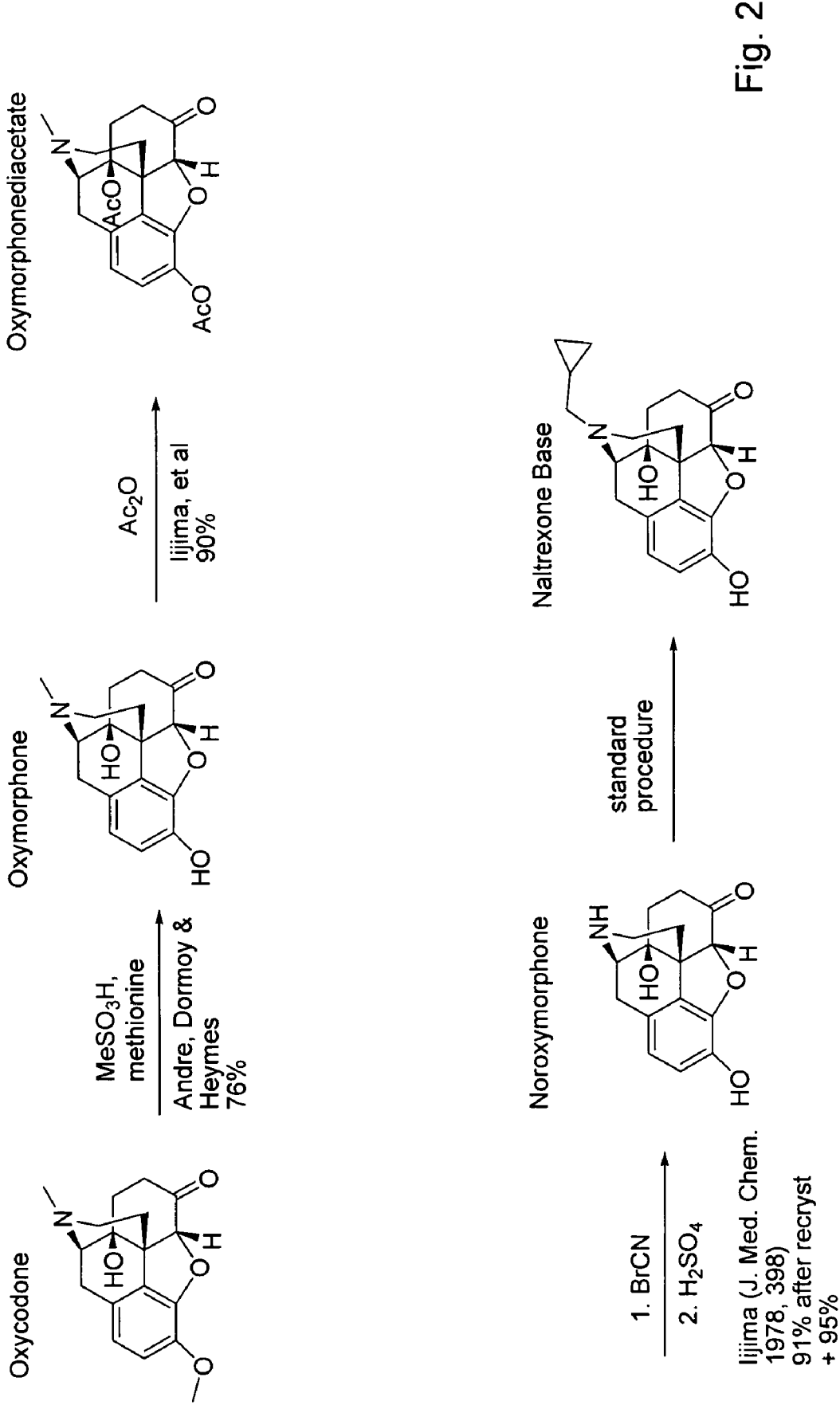

In order to give an overview over the improvements achieved by the present invention, it is referred to the enclosed FIGS. 1 and 2 showing two conventional ways for the synthesis of naltrexone base. Here, oxycodone is converted to acetyloxycodone in order to provide a protective group for 14 OH, and, then, demethylation is achieved by means of BrCN in order to achieve noroxycodone or noroxymorphone, respectively.

Figure 3:
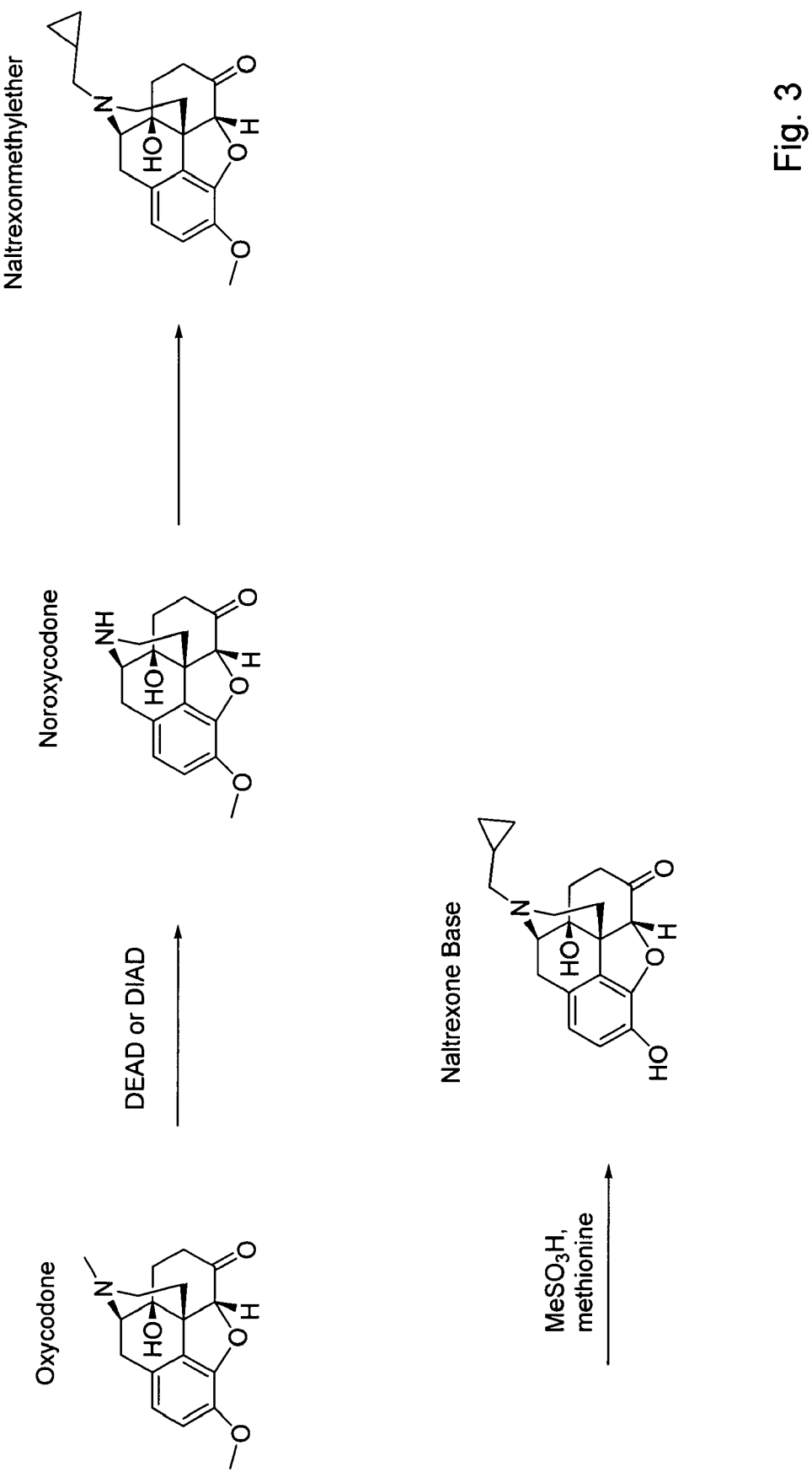

FIG. 3 describes the reaction of the present invention. Here, oxycodone is converted directly to noroxycodone, as it is also the case for oxymorphone to noroxymorphone (see FIG. 4).

It could be shown by the inventors that the yield of this reaction step is quite high, for example, for the conversion of oxymorphone to noroxymorphone the yield is about 80-90%.

DETAILED DESCRIPTION OF THE INVENTION

In particular, the present invention is directed to the following:
According to a first aspect, the invention is directed to a method of producing a compound of formula (I)

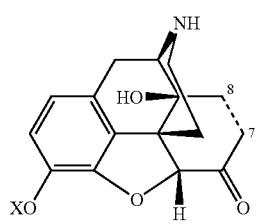

(I)

or a salt thereof, comprising
reacting a compound of formula (II)

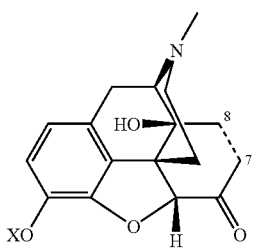

(II)

with an azodicarboxylic acid dialkyl ester of general formula $R^1OOC\!-\!N\!=\!N\!-\!COOR^2$ in a suitable solvent wherein
X is selected from H, alkyl, silyl or acetyl;
$R^1$ and $R^2$ are independently selected from linear or branched substituted or unsubstituted alkyl, preferably $C_1$-$C_6$-alkyl, more preferably methyl, ethyl, n-propyl, iso-propyl, n-butyl, sec-butyl, tert-butyl, pentyl, hexyl, benzyl, piperidyl; and wherein the bond between atoms 7 and 8 is a single or a double bond,
in order to obtain the compound of formula (I).

Salts of the above compound of formula (I) include carboxylate salts and others that are within a reasonable benefit/risk ratio, pharmacologically effective and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylale, mesylate, glucoheptonate, lactiobionate, and laurylsulfonate. See for example, S. M. Berge, et al., "Pharmaceutical Salts," J. Pharm. Sci., J. 977, 66:1-19, which is incorporated herein by reference.

The hydrochloride salt is preferred.

The azodicarboxylic acid dialkyl ester of formula $R^1OOC\!-\!N\!=\!N\!-\!COOR^2$ preferably is selected from compounds, wherein $R^1$ and $R^2$ are each ethyl or isopropyl, respectively, termed diethyl azodicarboxylate (DEAD) and diisopropyl azodicarboxylate (DIAD), or mixtures thereof.

In the reaction mixture, these compounds preferably are used in an amount of 1.5 to 3.0 eq.

In a further embodiment, the solvent is an aprotic polar or dipolar solvent and is preferably selected from methanol, ethanol, acetone, toluene, dimethylformamide, N,N-dimethylacetamide, acetonitrile, acetic acid ethylester and methyl-tert-butylether. Other solvents which fall into this category are methylene chloride, chloroform, tetrahydrofuran, dioxane, 1,3-dimethyl-2-imidazolidinone, dimethylsulfoxide, nitromethane or hexamethylphosphoric triamide. The starting material may be completely or partly dissolved within the aprotic polar or dipolar solvent.

The most preferred solvent is dimethylformamide.

The above demethylation reaction from a compound of formula (II) to a compound of formula (I) preferably is performed at a temperature in the range of room temperature (20° C.) to 100° C., preferably in the range of from 30-90° C., more preferably in the range of from 40-80° C. and most preferably, in the range of 50-70° C.

This temperature is maintained for at least one hour, preferably at least two hours, more preferably at least three hours and most preferably at least four hours.

In a further preferred embodiment, after reacting the compound of formula (II) with an azodicarboxylic acid dialkyl ester, the reaction solution is supplemented with 5,5-dimethylcyclohexane-1,3-dione (dimedone) or hydrazines and methanol.

The reason for using dimedone or hydrazines is that during the demethylation reaction an aminal is formed, which is hydrolized with methanol to yield the secondary amine (N—H) and formaldehyde-dimethylacetal (or formaldehyde following hydrolysation). In order to remove formaldehyde from the reaction mixture, a compound suitable for capturing the same will enhance the purity of the reaction. Any other compound suitable of capturing formaldehyde may be used in addition or in place of dimedone or a hydrazines.

Dimedone preferably is used in an amount of at least 2 Eq, for example 2-3.5 Eq regarding the presumed amount of formaldehyde (-dimethylacetal). An example of a preferred amount is about 3.0. Eq.

Preferably, the reaction solution is maintained at a temperature in the range of room temperature (20° C.) to 100° C., preferably in the range of 30-80° C., more preferably in the range of 40-70° C. over a time of 1-10 hours, preferably 2-5 hours after adding dimedone/hydrazines and methanol. A most preferred temperature range is 50-65° C.

In a further preferred embodiment, following reacting the compound of formula (II) and optionally reacting with dimedone and methanol, an acid is added to the reaction solution. The reason for adding an acid is to protonate the reaction product in order to bring it in the polar (water) phase. The remaining substances (for example DEAD or DIAD) are separated into the organic phase and, thus, removed.

In more detail, when the reaction of the compound of formula II with $R^1OOC\!-\!N\!=\!N\!-\!COOR^2$ is complete, an acid as mentioned above (for example hydrochloric acid), water and an organic solvent is added. The organic solvent is not restricted in its kind and is preferably methylenehloride. Thus, two phases arise, wherein the organic phase (for example methylenehloride) will incorporate the remaining amounts of $R^1OOC\!-\!N\!=\!N\!-\!COOR^2$ (DIAD or DEAD, for example) and formaldehyde/dimedone.

The aqueous phase in turn receives the reaction product as a hydrochloride, and, thus, is separating it from the reaction mixture.

Basically, any conceivable type of acid may be used for this purpose, however, hydrochloric acid turned out to be most promising. The hydrochloric acid preferably has a concentration of about 5% V/V.

In a preferred embodiment of the invention, the reaction solution further comprises at least one antioxidant. It was found that the addition an antioxidant can prevent the formation of oxidative by-products. In the inventive method, oxidative by-products can be formed, depending on the reaction conditions. The removal of these by-products might require additional purification steps. Especially difficult to remove are 2,2'-bis(14-hydroxy-14-methyl-4.5-epoxyrnorphinane-6-one)-derivatives which can only be removed by tedious purification procedures. In preferred embodiments, the amount of antioxidants in the reaction mixture is 1 to 50 mol-%, 5 to 40 mol-% or 10 to 30 mol-%. The addition of antioxidants can thus significantly improve the purity of the reaction product and reduce the process steps and costs of the reaction.

Suitable antioxidants are ascorbic acid and its derivatives, citric acid, tartric acid, polyhydroxy butyric acid (PHB) esters, butylated hydroxyanisol (BHA) and butylated hydroxytoluene (BHT), preferably 2,6-di-tert-butyl-4-methylphenol. Further suitable antioxidants are selected from the group consisting of organic acids and carboxylic acids, acid salts of amino acids, sodium metabisulphite, malic acid, isoascorbic acid, sodium sulphite, sodium bisulphate, tocopherol, water- and fat-soluble derivatives of tocopherol, sulphites, bisulphites and hydrogen sulphites, 2,6-di-t-butyl-alpha-dimethylamino-p-cresol, t-butylhydroquinone, di-t-amylhydroquinone, di-t-butylhydroquinone, butylhydroxytoluene, pyrocatechol, pyrogallol, propyl/gallate, and nordihydroguaiaretic acid, phosphoric acids, sorbic and benzoic acids, esters and derivatives thereof.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, materials, devices, articles or the like which has been included in the present specification is solely for the purpose of providing a context for the present invention.

The present invention now is described in more detail by means of Figures and Examples.

In the Figures, the following is shown:

FIG. 1 shows a reaction scheme showing one conventional way of the synthesis of naltrexone base. The demethylation step from acetyloxycodone to noroxycodone is done by means of conventional means (BrCN/$H_2SO_4$). The 14 OH-group is protected before the demethylation step is performed.

FIG. 2 shows a further reaction scheme showing one conventional way of the synthesis of naltrexone base. The demethylation step from acetyloxymorphone to noroxymorphone is done by means of conventional means (BrCN/$H_2SO_4$). The 14 OH-group is protected before the demethylation step is performed.

FIG. 3 shows a reaction scheme showing an example of the synthesis of the present invention. The demethylation step from acetyloxycodone to noroxycodone is done by means of DEAD or DIAD. The 14 OH-group is not protected before the demethylation step is performed.

Figure 4:
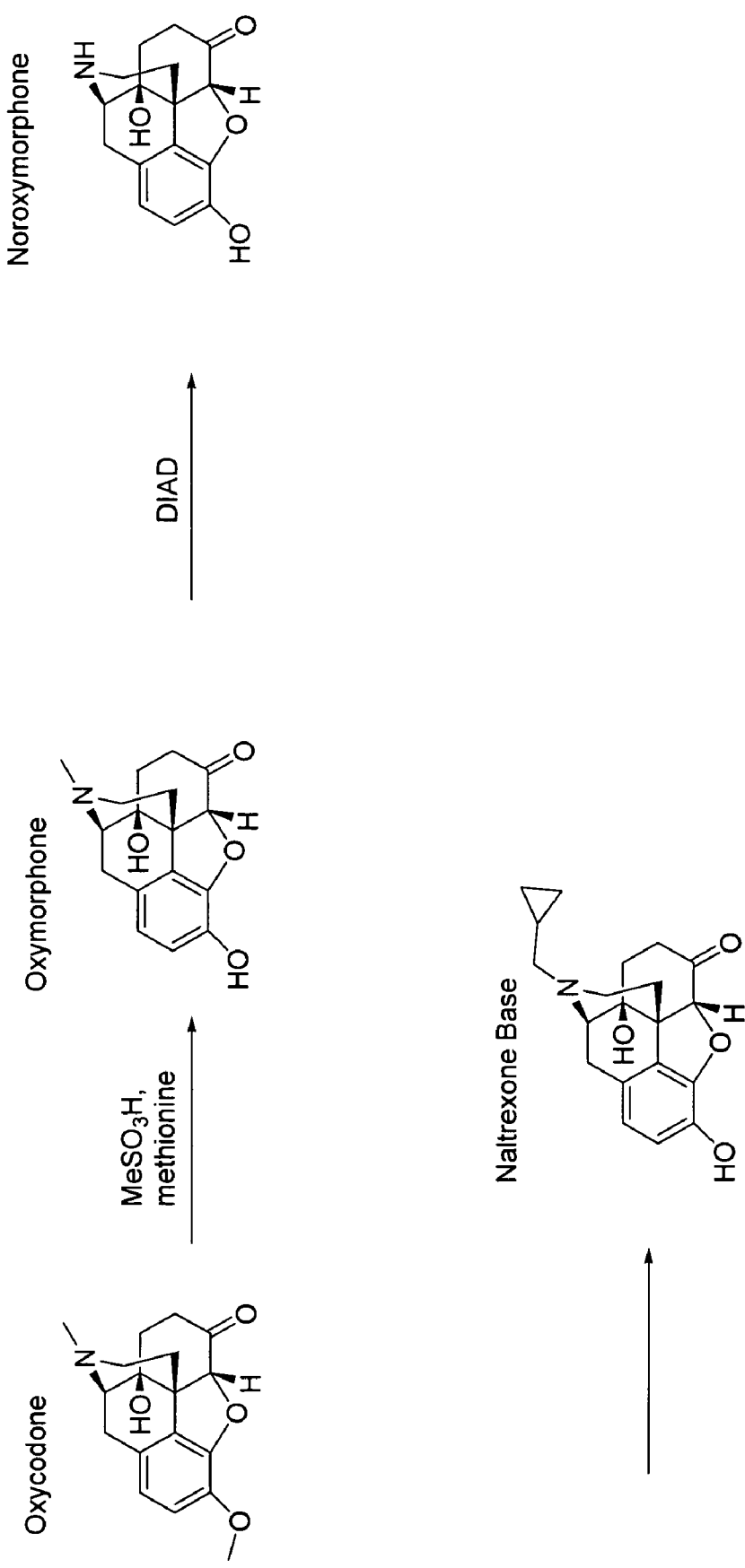

FIG. 4 shows a reaction scheme showing a further example of the synthesis of the present invention. The demethylation step from acetyloxymorphone to noroxymorphone is done by means of DEAD or DIAD. The 14 OH-group the like is not protected before the demethylation step is performed.

Figure 5:
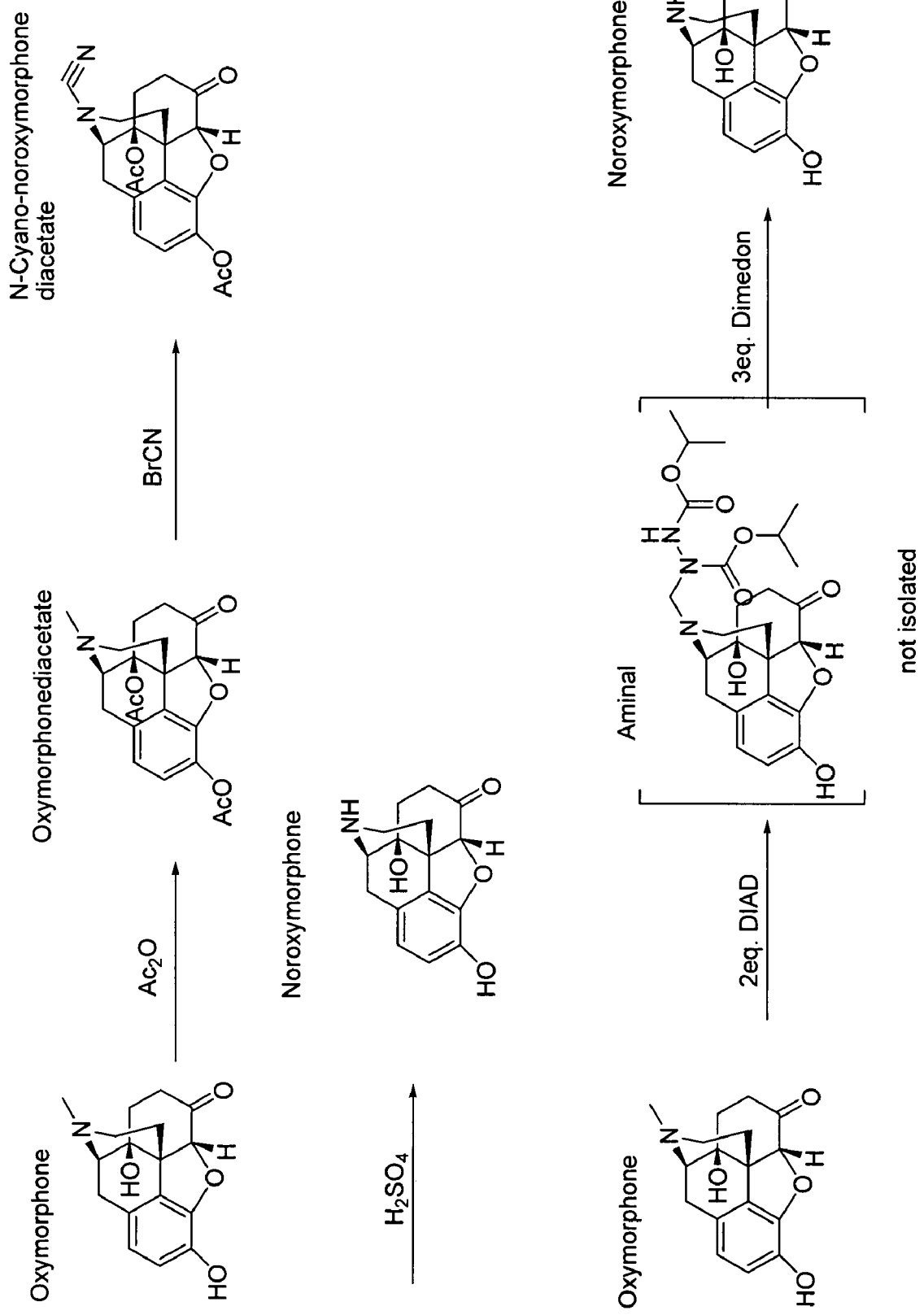

FIG. 5 shows a comparison of a way of synthesis according to a conventional approach ($1^{st}$ synthesis) and according to one embodiment of the present invention ($2^{nd}$ synthesis).

EXAMPLES

The following is an illustration of one way to carry out the invention. The Example is related to the demethylation of oxymorphone, however can also be performed for any conceivable compound reflected by formula (II).

N-Demethylation with an Azodicarboxylate:

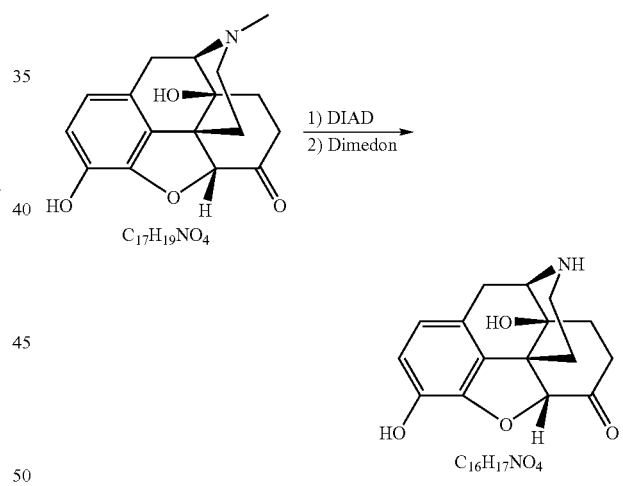

| Amount in g | Name of material | mmol | Content in % |
|---|---|---|---|
| | INPUT: | | |
| 50.0 | Oxymorphone | 154.8 | 93.3 w/w |
| 233.0 | Dimethyl formamide pure | | |
| 62.6 | Diisopropylazodicarboxylat (DIAD) | 309.6 | |
| 65.1 | 5,5-Dimethylcyclohexane-1,3-dione (Dimedone) | 464.3 | |
| 19.8 | Methanol pure | 618.8 | |
| 610.0 | Dichlormethane | | |
| 27.4 | Hydrochloride acid approximately 32% technical | 240.5 | 32 |
| 450.0 | Deionised water | | |

| | | -continued | | | |
|---|---|---|---|---|---|
| 26.2 | | Ammonia solution approximately 25%, pure | 384.6 | | 25 |
| 120.0 | | Acetone | | | |
| 1664.1 | | Sum | — | — | |

OUTPUT:

| Amount in g | Name of material | mol | Content in % | | 1 |
|---|---|---|---|---|---|
| 42.6 | Noroxymorphone | 130.3 | 87.9 | | 287.31 |

PROCESS:

| | | |
|---|---|---|
| 1 | 50.0 g | Oxymorphone are solved at room temperature in |
| | 233.0 g | dimethylformamide at room temperature and supplemented with |
| | 62.6 g | diisopropylazodicarboxylate. |
| | | The solution is heated to 55° C. and a yellow to red mixture is formed. |
| | | The solution is stirred for 4 hours at this temperature. |
| 2 | | Progress of the reaction is controlled by HPLC for example. |
| 3 | | To the reaction mixture |
| | 65.1 g | dimedone and |
| | 19.8 g | methanol are added starting at 55° C. |
| 4 | | The mixture is kept at a temperature of 60° C. whereas viscosity drops. |
| | | The reaction mixture is stirred for 4 hours at a temperature of 60° C. |
| 5 | | The reaction mixture is kept at a temperature of 20° C. and is supplemented with |
| | 460.0 g | dichlormethane, |
| | 200.0 g | deionised water and |
| | 27.4 g | hydrochloric acid 32% and is stirred for at least 5 min. |
| | | Two clear phases are formed: a redish organic and a yellow aqueous phase. |
| 6 | | The aqueous phase is separated. |
| 7 | | The aqueous phase is washed with |
| | 150.0 g | dichlormethane. The phases are separated. |
| 8 | | To the aqueous phase |
| | 26.2 g | aqueuos ammonia solution (25% w/w) are added at 20° C. under stirring. A suspension is formed. |

The further steps in the procedure comprise purification as used in chemistry. The steps described illustrate a possible way.

PURIFICATION:

| | | |
|---|---|---|
| 9 | | The suspension is brought to a temperature of 15° C. and stirred for at least two hours. |
| 10 | | The suspension is vacuum-filtered, dried and the residue is slurried with |
| | 250.0 g | water at a temperature of 20° C. |
| 11 | | The suspension is vacuum-filtered and dried well by aspiration. |
| 12 | | The filter residue is slurried with |
| | 100.0 g | acetone at a temperature of 20° C., vacuum-filtered and is dried well by aspiration. |
| 13 | | The filter residue is again washed with |
| | 20.0 g | acetone and well dried by aspiration. |
| 14 | | The product is dried in a vacuum drying oven at 60° C. |
| 15 | | 42.6 g product is yielded as a fawn solid. |

As it can be derived from table 1, showing the influence of the solvents and the amount of DIAD on the yield of demethylated products, dimethylacetamide, dimethylformamide and mixtures of dimethylformamide/toluene brought about the highest reaction yield. Further, the amount of DIAD used preferably was in the range of 1.5 to 3.0 eq.

TABLE 1

Noroxycodone: Examining the influence of the solvent and eq DIAD at 50° C.

| Solvent Solvent System | conc. of educt | eq DIAD | HPLC after | Educt | Product |
|---|---|---|---|---|---|
| Toluene | 10% | 1.6 | 2.5 h | 82.4% | 11.1% |
|  |  |  | 20 h | 19.7% | 61.4% |
| Toluene | 10% | 2.5 | 2.5 h | 72.2% | 26.2% |
|  |  |  | 20 h | 1.7% | 66.7% |
| Toluene | 10% | 4.1 | 2.5 h | 57.3% | 38.3% |
|  |  |  | 20 h | 0.00% | 79.8% |
| Acetone | 10% | 1.6 | 2.5 h | 72.1% | 25.0% |
|  |  |  | 20 h | 11.0% | 76.2% |
| Acetone | 10% | 2.5 | 2.5 h | 52.0% | 42.3% |
|  |  |  | 20 h | 0.00% | 86.0% |
| Acetone | 10% | 4.1 | 2.5 h | 36.0% | 56.1% |
|  |  |  | 20 h | 1.2% | 86.3% |
| Methanol | 10% | 1.6 | 2.5 h | 47.1% | 20.3% |
|  |  |  | 20 h | 37.3% | 8.5% |
| Methanol | 10% | 2.5 | 2.5 h | 3.0% | 41.6% |
|  |  |  | 20 h | 1.5% | 18.8% |
| Methanol | 10% | 4.1 | 2.5 h | 2.5% | 50.4% |
|  |  |  | 20 h | 1.4% | 20.0% |
| Ethanol | 10% | 1.6 | 2.5 h | 36.3% | 38.5% |
|  |  |  | 20 h | 2.1% | 31.8% |
| Ethanol | 10% | 2.5 | 2.5 h | 13.4% | 56.0% |
|  |  |  | 20 h | 0.00% | 26.0% |
| Ethanol | 10% | 4.1 | 2.5 h | 8.3% | 63.2% |
| MTBE | 10% | 3.0 | 16 h | 26.5% | 69.3% |
| DMF | 17% | 3.0 | 16 h | 1.0% | 86.3% |
|  |  |  | 42 h | 1.6% | 84.5% |
| DMAc | 17% | 3.0 | 16 h | 0.7% | 91.0% |
|  |  |  | 42 h | 0.5% | 92.5% |
| ACN | 17% | 3.0 | 16 h | 1.0% | 80.0% |
| EE | 17% | 3.0 | 16 h | 3.5% | 81.0% |
| Toluene | 33% | 2.0 | 16 h | 4.0% | 69.0% |
| Toluene | 7% | 2.0 | 16 h | 28.0% | 62.0% |
| Toluene | 33% | 4.0 | 16 h | 1.0% | 71.0% |
|  |  |  | 42 h | 1.0% | 58.0% |
| Toluene | 7% | 4.0 | 16 h | 7.0% | 79.0% |
| Toluene | 20% | 3.0 | 5 d 20° C. | 2.0% | 83.0% |
| DMF | 17% | 3.0 | 17 h | 1.0% | 79.0% |
| DMF | 10% | 3.0 | 17 h | 1.0% | 91.0% |
| DMF | 28% | 3.0 | 17 h | 1.0% | 85.0% |
| DMF | 17% | 2.0 | 17 h | 1.0% | 89.0% |
| 1DMF | 17% | 1.5 | 17 h | 1.0% | 89.0% |
| DMF/Toluene 6/1 (w/w) | 15% | 3.0 | 17 h | 1.0% | 88.0% |
| DMF/Toluene 1/1 (w/w) | 15% | 3.0 | 17 h | 1.0% | 86.0% |
| DMF/Toluene 1/6 (w/w) | 15% | 3.0 | 17 h | 2.0% | 85.0% |
| DMF/Toluene 1/1 (w/w) | 15% | 1.5 | 16 h | 0.0% | 89.0% |
| DMF/Toluene 1/1 (w/w) | 15% | 2.0 | 16 h | 1.0% | 89.0% |
| DMF/Toluene 1/6 (w/w) | 15% | 1.5 | 16 h | 11.0% | 76.0% |
| DMF/Toluene 1/6 (w/w) | 15% | 2.0 | 16 h | 3.0% | 83.0% |
| DMF/Toluene 1/1 (w/w) | 7% | 1.5 | 16 h | 4.0% | 90.0% |
| DMF/Toluene 1/1 (w/w) | 7% | 2.0 | 16 h | 0.0% | 92.0% |
| DMF/Toluene 1/6 (w/w) | 7% | 1.5 | 16 h | 23.0% | 70.0% |
| DMF/Toluene 1/6 (w/w) | 7% | 2.0 | 16 h | 12.0% | 81.0% |
| DMF | 15% | 1.0 | 16 h | 9.0% | 83.0% |
| Toluene dry | 7% | 2.0 | 20 h | 5.0% | 69.0% |
| Toluene/water 95/5 (w/w) | 7% | 2.0 | 20 h | 11.0% | 62.0% |
| DMF/water 98/2 (w/w) | 14% | 2.0 | 16 h | 0.7% | 79.7% |

Data indicated as analysed by HLPC.

TABLE 2

Noroxycodone: Examining the influence of the solvent and eq DEAD at 50° C.

| Solvent | conc. of educt | eq DEAD | HPLC after | Educt | Product |
|---|---|---|---|---|---|
| Toluene | 10% | 2.0 | 16 h | 10.0% | 64.0% |

Data indicated as analysed by HLPC.

TABLE 3

Noroxymorphone: Examining the influence of the solvent and eq DIAD at 50° C.

| Solvent | conc. of educt | eq DIAD | HPLC after | Educt | Product |
|---|---|---|---|---|---|
| DMF | 13% | 2.0 | 17 h | 4.6% | 89.1% |
| DMF | 13% | 2.0 | 16 h | 1.5% | 73.2% |

Data indicated as analysed by HLPC.

As shown in the table 4 below 2,2'-bisnoroxymorphone is formed as an unwanted side-product in the transformation of oxymorphone to noroxymorphone following the method described above. The amount of the by-products depends on the reaction conditions. In the presence of 25 mol-% of butylated hydroxytoluene (BHT), the formation of by-products, especially of 2,2'-bisnoroxymorphone, which is hard to remove otherwise, can be suppressed.

| Addition of BHT | Reaction time | Noroxymorphone (reaction product) | 2,2'-Bisnoroxymorphone (impurity) |
| --- | --- | --- | --- |
| Yes | 4 h | 92.6%*) | 0.0%*) |
| No | 4 h | 90.9% | 0.7% |
| Yes | 16 h | 92.7% | 0.0% |
| No | 16 h | 89.7% | 1.5% |

*) = area-% with HPLC

The invention claimed is:

1. A method of producing a compound of formula (I)

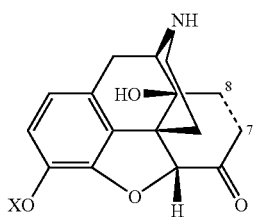

(I)

or a salt thereof, comprising:
reacting a compound of formula (II)

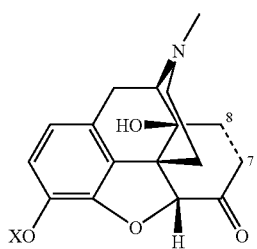

(II)

with an azodicarboxylic acid dialkyl ester of general formula $R^1OOC-N=N-COOR^2$ in a suitable solvent, and at least one antioxidant, wherein
X is selected from H, alkyl, silyl or acetyl; and
$R^1$ and $R^2$ are independently selected from a linear or branched substituted or unsubstituted alkyl, and
wherein the bond between atoms 7 and 8 is single or a double bond.

2. The method according to claim 1, wherein the solvent is an aprotic dipolar solvent.

3. The method according to claim 1, wherein the reaction is performed at a temperature in the range of from 20° C. to 100° C.

4. The method of claim 3, wherein the temperature is maintained for at least one hour.

5. The method of claim 1, wherein after reacting the compound of formula (II) with an azodicarboxylic acid dialkyl ester, the reaction solution is supplemented with 5,5-dimethylcyclohexane-1,3-dione (dimedone) and methanol or hydrazines and methanol.

6. The method of claim 5, wherein the reaction solution is maintained at a temperature in the range of from 20° C. to 100° C. over a time of 1-10 hours after adding dimedone and methanol.

7. The method according to claim 5, wherein following reacting the compound of formula (II) and optionally reacting with dimedone/hydrazines and methanol, an acid is added to the reaction solution.

8. The method of claim 7, wherein the acid is a hydrochloric acid.

9. The method according to claim 8, wherein the hydrochloric acid has a concentration of about 5% V/V.

10. The method according to claim 1, wherein the antioxidant is selected from the group consisting of ascorbic acid and its derivatives, citric acid, tartric acid, polyhydroxy butyric acid (PHB) esters, butylated hydroxyanisol (BHA) and butylated hydroxytoluene (BHT).

11. The method according to claim 1, wherein $R^1$ and/or $R^2$ are independently selected from a linear or branched, substituted or unsubstituted, $C_1$-$C_6$ alkyl.

12. The method according to claim 11, wherein $R^1$ and/or $R^2$ are independently selected from methyl, ethyl, n-propyl, iso-propyl, n-butyl, sec-butyl, tert-butyl, pentyl, and hexyl.

13. The method according to claim 12, wherein $R^1$ and/or $R^2$ are independently selected from isopropyl and ethyl.

14. The method according to claim 13, wherein $R^1$ and/or $R^2$ are identical.

15. The method according to claim 2, wherein the aprotic dipolar solvent is selected from the group consisting of methanol, ethanol, acetone, toluene, dimethylformamide, N,N-dimethylacetamide, acetonitrile, acetic acid ethylester and methyl-tert-butylether.

16. The method of claim 15, wherein the solvent is dimethylformamide.

17. The method according to claim 3, wherein the reaction is performed at a temperature in the range of from 30-90° C.

18. The method according to claim 3, wherein the reaction is performed at a temperature in the range of from 40-80° C.

19. The method according to claim 3, wherein the reaction is performed at a temperature in the range of from 50-70° C.

20. The method of claim 4, wherein the temperature is maintained for at least two hours.

21. The method of claim 4, wherein the temperature is maintained for at least three hours.

22. The method of claim 4, wherein the temperature is maintained for at least four hours.

23. The method of claim 6, wherein the reaction solution is maintained at a temperature in the range of from 20° C. to 100° C. for a period of time of from 2 to 5 hours after adding dimedone and methanol.

24. The method of claim 5, wherein the reaction solution is maintained at a temperature in the range of from 30 to 80° C. for a period of time of from 1 to 10 hours after adding dimedone and methanol.

25. The method of claim 24, wherein the reaction solution is maintained at a temperature in the range of from 30 to 80° C. for a period of time of from 2 to 5 hours after adding dimedone and methanol.

26. The method of claim 5, wherein the reaction solution is maintained at a temperature in the range of from 40 to 70° C. for a period of time of from 1 to 10 hours after adding dimedone and methanol.

27. The method of claim 26, wherein the reaction solution is maintained at a temperature in the range of from 40 to 70° C. for a period of time of from 2 to 5 hours after adding dimedone and methanol.

28. The method according to claim 10, wherein the antioxidant is 2,6-di-tert-butyl-4-methylphenol.

* * * * *